(12) United States Patent
Singhal et al.

(10) Patent No.: US 9,840,577 B2
(45) Date of Patent: Dec. 12, 2017

(54) ULTRA LOW DENSITY BIODEGRADABLE SHAPE MEMORY POLYMER FOAMS WITH TUNABLE PHYSICAL PROPERTIES

(71) Applicants: LAWRENCE LIVERMORE NATIONAL SECURITY, LLC, Livermore, CA (US); The Texas A&M University System, College Station, TX (US)

(72) Inventors: Pooja Singhal, Dublin, CA (US); Thomas S. Wilson, San Leandro, CA (US); Elizabeth Cosgriff-Hernandez, College Station, TX (US); Duncan J. Maitland, College Station, TX (US)

(73) Assignees: Lawrence Livermore National Security, LLC, Livermore, CA (US); The Texas A&M University System, College Station, TX (US)

( * ) Notice: Subject to any disclaimer, the term of this patent is extended or adjusted under 35 U.S.C. 154(b) by 0 days.

(21) Appl. No.: 15/269,516

(22) Filed: Sep. 19, 2016

(65) Prior Publication Data

US 2017/0002130 A1    Jan. 5, 2017

Related U.S. Application Data

(63) Continuation of application No. 13/797,631, filed on Mar. 12, 2013.

(60) Provisional application No. 61/651,477, filed on May 24, 2012.

(51) Int. Cl.
| | |
|---|---|
| C08G 18/10 | (2006.01) |
| C08G 18/32 | (2006.01) |
| C08G 71/04 | (2006.01) |
| C08G 18/66 | (2006.01) |
| A61B 17/00 | (2006.01) |
| C08G 63/00 | (2006.01) |
| C08G 63/685 | (2006.01) |
| C08J 9/00 | (2006.01) |
| C08G 18/08 | (2006.01) |
| C08G 18/16 | (2006.01) |
| C08G 18/73 | (2006.01) |
| C08G 101/00 | (2006.01) |

(52) U.S. Cl.
CPC ...... *C08G 18/6622* (2013.01); *A61B 17/0057* (2013.01); *C08G 18/10* (2013.01); *C08G 18/14* (2013.01); *C08G 18/165* (2013.01); *C08G 18/73* (2013.01); *C08G 63/00* (2013.01); *C08G 63/6852* (2013.01); *C08G 71/04* (2013.01); *C08J 9/00* (2013.01); *A61B 2017/00592* (2013.01); *A61B 2017/00606* (2013.01); *A61B 2017/00623* (2013.01); *C08G 2101/005* (2013.01); *C08G 2101/0083* (2013.01); *C08G 2230/00* (2013.01); *C08G 2280/00* (2013.01); *C08J 2375/06* (2013.01)

(58) Field of Classification Search
CPC ........ C08G 18/10; C08G 18/14; C08G 63/00; C08G 71/04; C08G 18/3271
See application file for complete search history.

(56) References Cited

U.S. PATENT DOCUMENTS

| | | | |
|---|---|---|---|
| 3,989,676 A | 11/1976 | Gerkin et al. | |
| 4,990,545 A * | 2/1991 | Hourai | B29C 61/003 427/261 |
| 5,571,857 A | 11/1996 | Gruber et al. | |
| 5,770,635 A | 6/1998 | Lee et al. | |
| 5,986,039 A | 11/1999 | O'Brien et al. | |
| 2003/0236314 A1 | 12/2003 | Haider et al. | |
| 2006/0036045 A1* | 2/2006 | Wilson | B82Y 30/00 525/452 |
| 2009/0253816 A1 | 10/2009 | Nascimento et al. | |
| 2009/0313909 A1 | 12/2009 | Clatty et al. | |
| 2011/0039967 A1* | 2/2011 | Wilson | B82Y 30/00 521/164 |

(Continued)

FOREIGN PATENT DOCUMENTS

| | | | | |
|---|---|---|---|---|
| WO | 2006098757 | 9/2006 | | |
| WO | WO 2011085847 A1 * | 7/2011 | | A61L 27/50 |

OTHER PUBLICATIONS

Meier, et al., "Synthesis and Characterization of 4- and 6-arm Star-Shaped Poly(E-Caprolactone)s", e-Polymers, 2005, vol. 85. pp. 1-8.

(Continued)

*Primary Examiner* — Kara Boyle
(74) *Attorney, Agent, or Firm* — Eddie E. Scott

(57) ABSTRACT

Compositions and/or structures of degradable shape memory polymers (SMPs) ranging in form from neat/unfoamed to ultra low density materials of down to 0.005 g/cc density. These materials show controllable degradation rate, actuation temperature and breadth of transitions along with high modulus and excellent shape memory behavior. A method of m ly low density foams (up to 0.005 g/cc) via use of combined chemical and physical aking extreme blowing agents, where the physical blowing agents may be a single compound or mixtures of two or more compounds, and other related methods, including of using multiple co-blowing agents of successively higher boiling points in order to achieve a large range of densities for a fixed net chemical composition. Methods of optimization of the physical properties of the foams such as porosity, cell size and distribution, cell openness etc. of these materials, to further expand their uses and improve their performance.

10 Claims, 4 Drawing Sheets

(56) References Cited

U.S. PATENT DOCUMENTS

2011/0275726 A1\* 11/2011 Wilson .................. C08G 18/83
                                                         521/50.5
2012/0018922 A1    1/2012 Kratz et al.
2012/0308804 A1\* 12/2012 Lendlein ................ A61L 27/50
                                                         428/221

OTHER PUBLICATIONS

Sivakumar et al., "Poly(ϵ-caprolactone)-basedhyperbranched polyurethanes prepared via A2 + B3 approach and its shape memory behavior," from European Polymer Journal 45, Elsevier, 2009, pp. 2329-2337.
European Search Report for EP Application No. 13794314.8, corresponding to PCT/US13/041894, 8 pages.
International Search Report and Written Opinion for PCT/US13/041894, corresponding to U.S. Appl. No. 13/797,631, 11 pages.
European Search Report for EP Application No. 13794314.8, corresponding to U.S. Appl. No. 15/269,516, 4 pages.
European office action for EP Application No. 13794314.8, dated Aug. 4, 2017, corresponding to U.S. Appl. No. 15/269,516, 3 pages.
European Patent Office, Communication Pursuant to Article 94(3) EPC dated Aug. 4, 2017, in European Patent Application No. 13794314.8.

\* cited by examiner

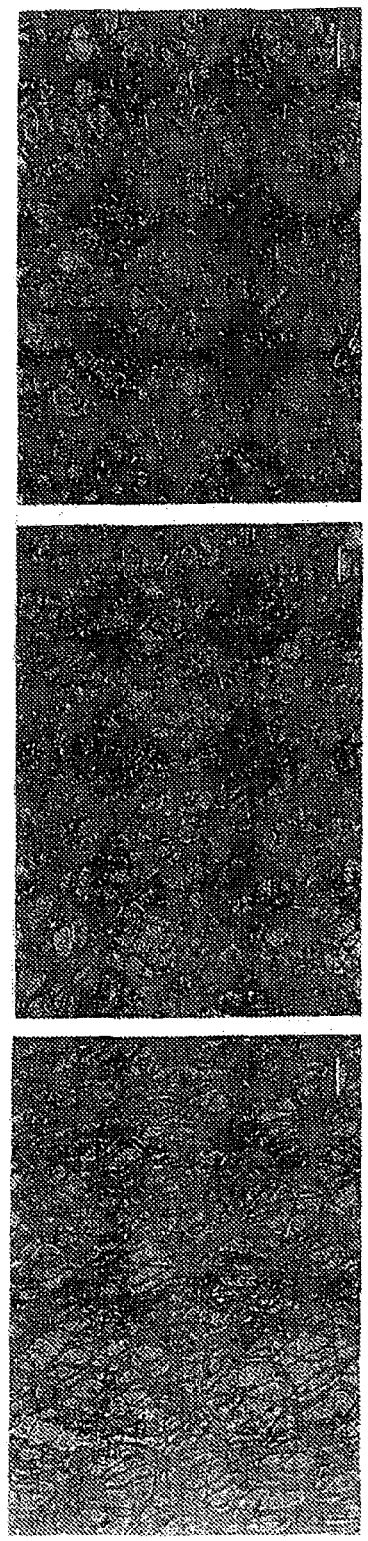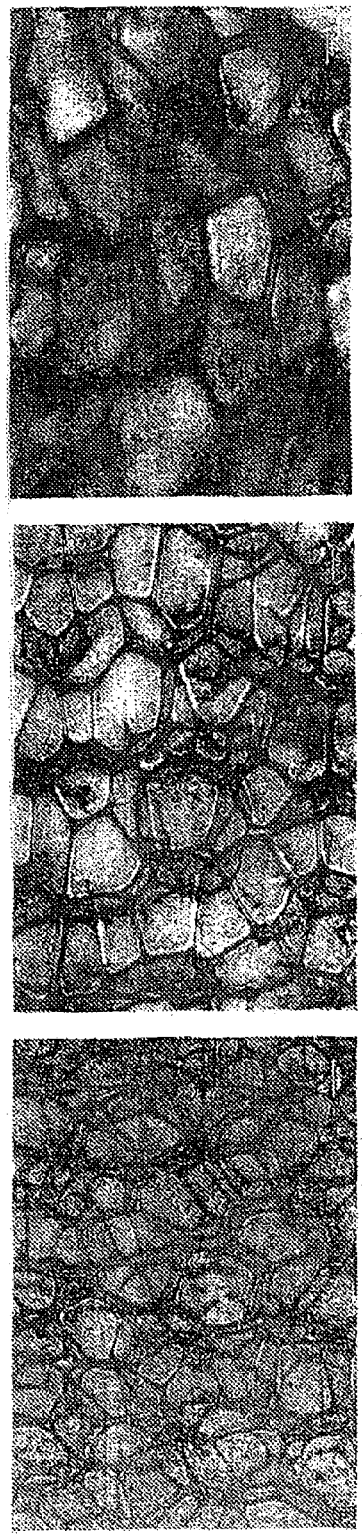
FIG. 5A  FIG. 5B  FIG. 5C  FIG. 5D  FIG. 5E  FIG. 5F

ULTRA LOW DENSITY BIODEGRADABLE SHAPE MEMORY POLYMER FOAMS WITH TUNABLE PHYSICAL PROPERTIES

This application is a Continuation of Co-pending U.S. Non-Provisional patent application Ser. No. 13/797,631 filed Mar. 12, 2013, titled, "Ultra-Low Density Biodegradable Shape Memory Polymer Foams with Tunable Physical Properties," which claims priority based upon U.S. Provisional Patent Application No. 61/651,477 filed May 24, 2012, titled, "Ultra-Low Density Biodegradable Shape Memory Polymer Foams with Tunable Physical Properties." Both of the above disclosures are hereby incorporated by reference in their entirety for all purposes. This invention was made with government support under EB000462 awarded by National Institutes of Health. The government has certain rights in the invention.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

Field of Endeavor

This invention relates to shape memory polymers and specifically to shape memory polymers and polymer foams having enhanced characteristics of degradability, control over cell structure, and density.

State of Technology

Shape memory polymers (SMPs) are materials which can remember two or more shapes, and can be actuated to go from one shape to another via a stimuli involving heat or light etc. Thermally responsive SMPs that use heat energy for their actuation can be deformed from their primary shape to a secondary shape above their actuation temperature. This secondary shape can then be "fixed" by cooling the deformed shape to below the material's actuation temperature. When they are heated to above their actuation temperature on demand, they recover their "remembered" primary shape. Polyurethane based SMP foams were initially proposed by Hayashi et. al—Japanese patent 5049591 (1991). Other related patent applications were also filed in this field by Applicants, U.S. patent application Ser. No. 10/801,355 (2004) and U.S. patent Patent Application number 20060036045 (2005). These shape memory materials are useful in diverse applications like shape adaptive sportswear (helmets, suits), housing (thermal sealing of doors and windows) and robotics (conformal grip design). Also these materials are being investigated for use in automobile and aerospace industries for self healing automobile bodies and morphing aircraft wings. In addition, shape memory foam based biomedical devices for minimally invasive surgeries are being developed, see El Feninat, F., Laroche, G., Fiset, M. & Mantovani, D. Shape memory materials for biomedical applications. *Advanced engineering materials* 4, 91-104 (2002); Sokolowski, W., Metcalfe, A., Hayashi, S., Yahia, L. H. & Raymond, J. Medical applications of shape memory polymers. *Biomedical Materials* 2, S23 (2007) and Small, W. et al. Shape memory polymer stent with expandable foam: a new concept for endovascular embolization of fusiform aneurysms. *Biomedical Engineering, IEEE Transactions on* 54, 1157-1160 (2007).

Introducing degradability is a key requirement for the development of a SMP either as a biomedical device to avoid long term presence of a foreign material in the human body, or for the ecological concerns of using polymeric materials. Lendlein, A. & Langer, R. Biodegradable, elastic shape-memory polymers for potential biomedical applications. *Science* 296, 1673 (2002) Several degradable SMPs have been reported with polycaprolactone diol, lactide and glycolide moieties. Caprolactone has been used copiously in the biodegradable applications and its degradation products have been shown to be benign in the earlier biocompatibility studies; Rickert, D., Lendlein, A., Kelch, S., Franke, R. & Moses, M. Cell proliferation and cellular activity of primary cell cultures of the oral cavity after cell seeding on the surface of a degradable, thermoplastic block copolymer. *Biomedizinische Technik. Biomedical engineering* 50, 92 (2005).

However, most of these materials reported earlier are either linear polymers, have relatively low covalent crosslink density, or are based on physical crosslinks, which can limit the mechanical and/or shape memory behavior of the material.

In contrast to above, a network structure consisting of high density of covalent crosslinks, is preferable for good mechanical properties and improved shape memory behavior (high recovery force, high shape recovery), particularly for very low density foams. This is so because, firstly, the modulus of a foamed material declines rapidly as its density is reduced: $E_{porous}=E_{neat}[Q_{porous}/Q_{neat}]$ for open cell foams, where $E_{porous}$ and $E_{neat}$ are the Young's moduli and $Q_{porous}$ and $Q_{neat}$ are the densities, of porous and neat/unfoamed materials respectively. Hence for very low density materials to have good mechanical properties, they should be based on neat/unfoamed materials with significantly high modulus i.e. high density of crosslinks (from $E \sim 3n_cRT$ where E is the Young modulus of material, $n_c$ the number of active network chain segments per unit volume, R is the ideal gas constant and T is the Temperature). Secondly, it is important to have a covalently crosslinked structure, rather than a physically crosslinked structure for improved shape memory behavior to be retained over extended periods of time, i.e. to avoid secondary-shape forming phenomenon as is noticed in some physically crosslinked materials; Tobushi, H., Matsui, R., Hayashi, S. & Shimada, D. The influence of shape-holding conditions on shape recovery of polyurethane-shape memory polymer foams. *Smart materials and structures* 13, 881 (2004). Since physical crosslinks are labile, entropically driven polymer chains in a physically crosslinked material can move in and out of their crosslink sites to attain a more preferable, lower energy equilibrium conformation. This causes the material to lose the memory of its primary shape, and thus, lose its ability to actuate under a stimulus (as noticed in the secondary-shape forming phenomenon). In contrast, covalent/chemical crosslinks do not allow such rearrangement of entropically driven polymer chains, and thus ensure improved shape memory behavior even after extended periods of storage in the secondary shape. Hence a high crosslink density in the network structure, and use of chemical/covalent crosslinks for achieving the same, form the basis of the materials of this invention.

The method of synthesis of such a highly covalently crosslinked degradable polymer network based on polyurethane chemistry is an embodiment of this invention. Degradability is shown using multifunctional Polycaprolactone based hydroxyl monomers, which has not been proposed before in blown foams. Also other variations of monomers for developing a highly crosslinked network structure are disclosed as are methods of controlling material's actuation temperature and rate of degradation.

Controlling the cell structure of foams is another key requirement in generation of commercial grade SMP foams, and we propose manipulating viscosity of the foaming solution for the same. The effect of viscosity on foam cell structure has been studied in detail for foam emulsions; Kim, Y. H., Koczo, K. & Wasan, D. T. Dynamic Film and Interfacial Tensions in Emulsion and Foam Systems. *Journal of colloid and interface science* 187, 29-44 (1997) and Shah, D., Djabbarah, N. & Wasan, D. A correlation of foam stability with surface shear viscosity and area per molecule in mixed surfactant systems. *Colloid & Polymer Science* 256, 1002-1008 (1978)[19-20] and in HIPE foam synthesis procedure; Busby, W., Cameron, N. R. & Jahoda, C. A. B. Emulsion-Derived Foams (PolyHIPEs) Containing Poly (-caprolactone) as Matrixes for Tissue Engineering. *Biomacromolecules* 2, 154-164 (2001) and Christenson, E. M., Soofi, W., Holm, J. L., Cameron, N. R. & Mikos, A. G. Biodegradable Fumarate-Based PolyHIPEs as Tissue Engineering Scaffolds. *Biomacromolecules* 8, 3806-3814, doi: 10.1021/bm7007235 (2007). For blown foams, the indirect effect of change in viscosity on cell structure, via changing the functionality of polyols or chemistry of foams[24] has been reported; Tabor, R., Lepovitz, J., Potts, W., Latham, D. & Latham, L. The effect of polyol functionality on water blown rigid foams. *Journal of Cellular Plastics* 33, 372 (1997).

However, using this technique to control the cell structure of very low density blown foams, keeping the net chemical composition the same has not been previously reported. Currently in literature, low density foams have been reported mostly down to the lower limit of 0.02-0.03 g/cc; see Thirumal, M., Khastgir, D., Singha, N. K., Manjunath, B. & Naik, Y. Effect of foam density on the properties of water blown rigid polyurethane foam. *Journal of Applied Polymer Science* 108, 1810-1817 (2008) and Simpson, S. S. & Sato, et al, U.S. Pat. No. 7,338,983 (2008).

A recent patent by Burdeniuc reported making foams down to 0.006 g/cc, but a staggering 75 wt % water was used in synthesis; Burdeniuc, J. J. & Andrew, G. D. Catalyst composition for water blown, low density, rigid polyurethane foam, US patent application 20100152312 (2008). Since use of high amounts of water as chemical blowing agent will interfere with the intended covalently crosslinked network structure of the material, this is not a preferred route. Another patent reported densities down to 0.016 g/cc by varying the polyol type and amount; Haider, K. W. et al. Polyol compositions useful for preparing dimensionally stable, low density water-blown rigid foams and the processes related thereto, U.S. Pat. No. 7,300,961 (2007). However, keeping the same chemical composition, large variation in densities with lower limit ~0.005 g/cc has not been reported before.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

It is an object of the present invention to provide compositions and/or structures of degradable SMPs ranging in form from neat/unfoamed to ultra low density materials of down to 0.005 g/cc density. These materials show controllable degradation rate, actuation temperature and breadth of transitions along with high modulus and excellent shape memory behavior.

It is another object of the present invention to provide a method of controlling the cell structure of polymer foams by controlling the prepolymer viscosity and other related methods.

It is still another object of the present invention to provide a method of making extremely low density foams (up to 0.005 g/cc) via use of combined chemical and physical blowing agents, where the physical blowing agents may be a single compound or mixtures of two or more compounds, and other related methods, including of using multiple co-blowing agents of successively higher boiling points in order to achieve a large range of densities for a fixed net chemical composition.

It is yet another object of the present invention to provide methods of optimization of the physical properties such as porosity, cell size and distribution, cell openness etc. of these materials, to further expand their uses and improve their performance.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

FIGS. 5A through 5F show "Variation in cell structure achieved based on the viscosity of the foaming prepolymer".

DETAILED DESCRIPTION OF SPECIFIC EMBODIMENTS

Figure 1:
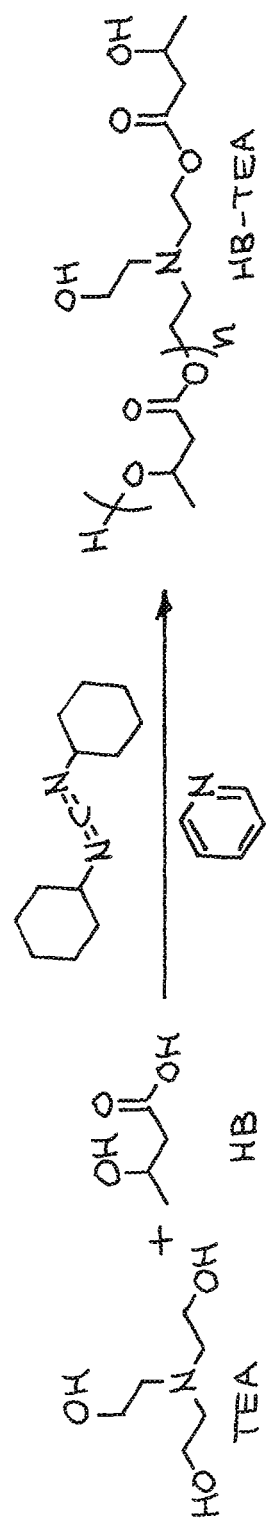
FIG. 1 is a synthesis outline for making a trifunctional hydroxyl monomer with ester linkages from triethanol amine and 3-hydroxybutyrate.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The present invention consists of compositions and methods for degradable shape memory polymer (SMP) and foams from those polymers. It is also methods for controlling the properties of these SMPs. The invention may be expressed in four broad embodiments that include:

1: Compositions and/or structures of degradable SMPs ranging in form from neat/unfoamed to ultra low density materials of down to 0.005 g/cc density.

2: Method of controlling the cell structure of polymer foams from the polymers of embodiment 1.

3: Method of making extremely low density foams (up to 0.005 g/cc) by using combined chemical and physical blowing agents, wherein the physical blowing agents consist of one or more co-blowing agents and other related methods, and 4: Methods of optimization of the physical properties such as porosity, cell size and distribution, cell openness etc. of these materials.

General Embodiment 1: Compositions and/or Structures of Degradable SMPs Ranging in Form from Neat/Unfoamed to Ultra Low Density Materials of Down to 0.005 g/Cc Density.

This embodiment included compositions that show controllable degradation rate, actuation temperature and breadth of transitions along with high modulus and excellent shape memory behavior. The materials disclosed here are degradable, with good mechanical properties and shape memory behavior at very low densities. One of the ingredients for making these materials is a multifunctional hydroxyl, amine, or carboxylic acid containing monomer of small molecular weight (e.g. 200-1500 g), having degradable (for e.g. ester, ether, amide, urethane) linkages. Such monomers can be crafted by any of the following schemes:

1. As shown in FIG. 1—Using a branched monomer (3 or more branches in structure) with hydroxyl end groups and reacting it with a difunctional monomer with an acid group on one end and a hydroxyl group on the other end. Reaction of the hydroxyl group of branched monomer and acid group of difunctional monomer will form an ester linkage releasing a water molecule. This will extend the branches of the original branched hydroxyl monomer with ester linkages, keeping the hydroxyl group as its terminal/end group.

Figure 2:
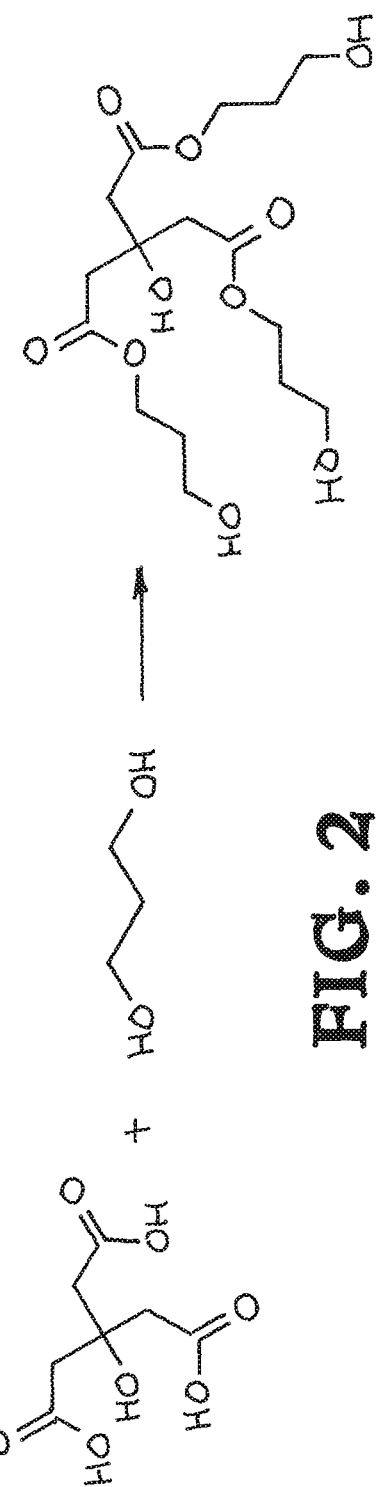
FIG. 2 is a synthesis outline for making a tetrafunctional hydroxyl monomer with ester linkages from Citric Acid and 1, 3 Propane diol.

2. As shown in FIG. 2—Alternatively, a branched monomer with acid end groups can be reacted with a difunctional monomer containing hydroxyl end groups. This will similarly form a multifunctional monomer having ester linkage with the end groups of hydroxyl functionality.

3. Reaction of branched polyol with di-carboxylic acid, resulting in an polycarboxylic acid monomer containing ester linkages.

4. Steps described in (2) and (3) may be accomplished in succession to controllably increase the number of degradable functional groups in each arm of the monomer, which in turn provides a means to control degradation kinetics.

By scheme 1 (FIG. 1) some of the possible multifunctional hydroxyl monomers include Triethanol amine (TEA), Hydroxy propyl ethylene diamine (HPED), Glycerol, Pentaerythritol or Trimethylolpropane, Bis-tris methane, Bis-tris propane, 1, 2, 4 Butane triol, Miglitol, Trimethylolethane and Tris(hydroxymethyl)aminomethane.

Some of the possible monomers with one acid and (at least one) hydroxyl group, that can react with above multifunctional hydroxyl groups include L-Threonic acid, Tricine, Shikimic acid, 3-Hydroxybutyrate, ϵ-Caprolactone, Lactic acid, and Glycolic acid.

By scheme 2 (FIG. 2), multifunctional carboxylic acids can include 1,4-benzoquinonetetracarboxylic acid, Ethylenediamine-N,N'-disuccinic acid, furantetracarboxylic acid, hydroxycitric acid, citric acid, Nitrilotriacetic acid, Aconitic acid, isocitric acid and Propane-1,2,3-tricarboxylic acid.

Some of the possible diol monomers that can react with above multifunctional carboxylic acids by scheme 2, include Polyethylene glycol, 1,3-Propanediol, 1,4-Butanediol, 1,5-Pentanediol, 1,2-Propanediol, 1,2-Butanediol, 2,3-Butanediol, 1,3-Butanediol, 1,2-Pentanediol, Etohexadiol and 2-Methyl-2,4-pentanediol.

In one embodiment of the suggested synthesis by scheme 1, Triethanol amine is end capped with 3-Hydroxybutyrate (HB) as shown in FIG. 1. Anhydrous pyridine is used to initiate the formation of an ester link between the hydroxyl end groups of TEA and the activated carboxyl group of the HB. The precipitated dicyclohexylurea is then removed with vacuum filtration and the polymer solution is washed with distilled water. Solvent is then removed by rotary evaporation, followed by the drying of the polymer in vacuum.

In another embodiment of suggested synthesis by scheme 2, a tetrafunctional hydroxyl monomer is prepared by end capping Citric acid (CA) with 1, 3 Propane diol, as shown in FIG. 2. CA and Propane diol are reacted together at 160° C. under stirring for 15 minutes. The temperature is subsequently decreased to 140° C. and reaction mixture is stirred for 1 hour. The resulting prepolymer is purified by precipitation in water and then it is freeze dried. While the idea of making these highly crosslinkable short-branch multifunctional monomers using 1, 3 Propane diol is new, a similar synthesis procedure involving citric acid and its derivatives has been adopted by Yang et. al. and group[29].

In a yet another embodiment of the suggested synthesis by scheme 1, Polycaprolactone triol (PCT) obtained from grafting ϵ-Caprolactone on Trimethylolpropane is used.

It is to be emphasized that some such monomers are available commercially, such as PCT, but several others can be made under this scheme, and be used for the synthesis of the highly crosslinked materials which form the subject of this invention.

These branched monomers with end hydroxyl functionality, as achieved from above processes, are then reacted with small molecular weight diisocyanate monomers. These include (but are not limited to), Hexamethylene diisocyanate (HDI), Tri-methyl Hexamethylene diisocyanate (TMHDI) and Isophorone diisocyanate for aliphatic options and monomers such as Toluene diisocyanate, Methylene diphenyl diisocyanate for aromatic options.

Making polymers in neat/unfoamed form: For making neat polymers, stoichiometric amounts of hydroxyl monomer and diisocyanate are mixed together and stirred until a clear one phase solution is formed. Thereafter the solution is further degassed, cast into molds and allowed to cure. In neat/unfoamed form, these heavily crosslinked materials are an optically clear polymer due to their amorphous structure, have a good shape memory and are degradable.

The ease of forming a single phase solution with more hydrophobic HDI and TMHDI decreases with increase in the hydrophilicity of the branched hydroxyl monomers, such as with incorporation of poly caprolactone triol or TEA in the synthesis. A speed mixer such as Flacktek, Thinky or another vigorous mixing technique is utilized for this purpose. Mixing over a range of 10 minutes to over an hour at 3000-4000 rpm can be required depending on the content of the more hydrophilic monomer in the formulation.

For reducing the degradation rate, other multifunctional polyols mentioned above, without degradable linkages can be substituted for hydroxyl monomers with degradable linkages in material synthesis. Alternatively, the number of degradable linkages can be reduced in each branch of the hydroxyl monomers. On the extreme end, all the used monomers can be without a degradable linkage e.g. TEA, HPED and Glycerol etc. to give stable/non-degradable materials.

For maintaining the same glass transition/actuation temperature, while changing the degradation rate of the materials, hydroxyl monomers without degradable linkages are chosen such that their steric hindrance and mobility is comparable to that of monomers with degradable linkages. These non-degradable branched hydroxyl monomers are then substituted for the degradable branched hydroxyl monomers in appropriate amounts.

EXAMPLE 1

As the ratio of Polycaprolactone triol based monomer (Mw 300 g) is increased in the polyurethane based on HDI and TEA, HPED and PCT, the rate of degradation of the material is increased. As part of the trifunctional caprolactone based monomer is substituted with tetrafunctional non-degradable monomer such as HPED, the glass transition of material increases, and rate of degradation decreases. On the other hand, as the trifunctional caprolactone based monomer is substituted with a trifunctional non-degradable monomer such as TEA, the change in glass transition is not very noticeable, and significant decrease in rate of degradation can be achieved.

Controlling the length of the network active chains in the polymer structure can define the breadth of the transition of the materials from their glassy to rubbery state. The wider the distribution of lengths of network active chains in the polymer, the broader will be the transitions of glass transition temperature, modulus etc. A narrow distribution on the other hand, will give sharper transitions. One of the ways to achieve this is by controlling the length of each branch of the multifunctional monomers, for e.g. by controlling the number of hydrolysable linkages in each branch.

Similarly, controlling or keeping the same number of degradable linkages in each arm of the multifunctional monomers will give a sharper drop in mass and more reproducible mass loss pattern with respect to time during the degradation of the material. A more broad distribution of the number of degradable linkages in each arm, or in each network active chain segment across the sample, will lead to a more spread out/or broader drop in mass with respect to time.

Making polymers as low density foams: For making foams, first a prepolymer is made with excess isocyanate in the desired ratio of hydroxyl monomers based on degradability and actuation temperature requirements. The solutions are mixed until a clear, single phase is formed, possibly requiring the use of a Flacktek/Thinky speed mixer or an equivalent high speed mixing technique, based on the content of more hydrophilic moieties, such as Poly caprolactone triol and Triethanol amine. The prepolymers are then allowed to cure over a 2-3 day period. Typically prepolymer viscosities in the range of 2 Pa.s to 60 Pa.s post cure, can potentially yield viable foams.

In the second step for making foams, the balance hydroxyl monomers in the desired ratio of functionality and degradability are mixed together with surfactants, tin and amine based catalysts, and water. Water here accounts for a percentage of hydroxyl monomers via urea formation and assists in the chemical blowing of foam. This hydroxyl premix is added to the prepolymer with excess isocyanate in calculated amounts, and mixed vigorously, optionally in a speed mixer, for a few seconds. Then a physical blowing agent (or a combination of physical blowing agents) is added and solution is mixed again. Thereafter the foam is allowed to rise in an oven at 90° C. The high temperature helps in maximizing the generation of $CO_2$ via the chemical blowing reaction in the foaming solution.

While some process details are provided in the disclosure above, several specifics such as choice of surfactants and catalysts, the order of mixing the components together, mixing durations and speeds, cure temperature and conditions can be modified/changed with similar results.

Instead of using a polyurethane chemistry, multifunctional monomers with other functional end groups that are reactive with isocyanates, such as amines and carboxylic acids etc. can also be used. Further, these materials can be modified by use of a variety of additives and/or fillers, such as contrast agents, plasticizers, dyes, pigments, carbon nanotubes etc., to enhance/change its physical, mechanical, optical, electrical, or magnetic properties. In addition to above, several post synthesis processes for reticulation etc. such as hydrolysis, oxidation, application of pressure, heat or mechanical treatment, can be performed on the foams to modify their physical structure.

EXAMPLE 2

Degradable foams were made by using Polycaprolactone triol as the degradable hydroxyl monomer made from grafting caprolactone moieties on Trimethylolpropane by the first scheme detailed above (used as received from Sigma Aldrich, Mw 300 g), Triethanol amine as the non-degradable hydroxyl monomer to control the rate of degradation, and Hexamethylene diisocyanate.

First an NCO premix, or prepolymer with excess diisocyanate, is made by mixing the components as per Table 1. The mixing is performed in a Flacktek speed mixer or an equivalent vigorous mixing technique as both Polycaprolactone triol and Triethanol amine are not readily miscible in Hexamethylene diisocyanate. After a clear solution is formed, the NCO premix is stored under Nitrogen atmosphere and allowed to cure over a period of 2-3 days. The viscosity of the solution increases as reaction occurs between hydroxyl and isocyanate groups, reaching a value in the range of 2-60 Pa.s.

Figure 3A:
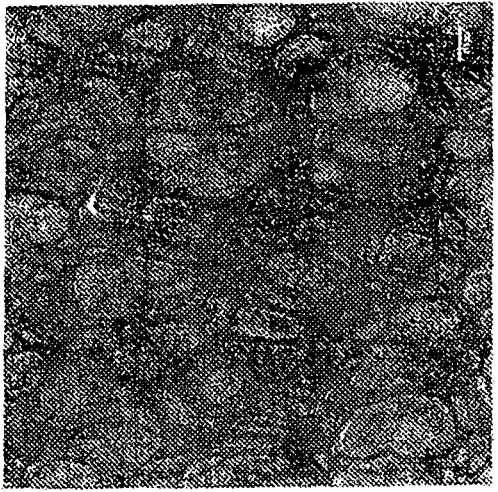
FIGS. 3A, 3B and 3C are displays pictures of cell structure of low density degradable shape memory polymer foams of the invention.
Figure 3B:
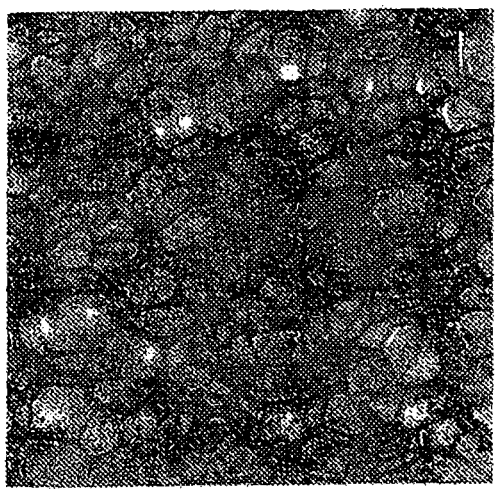
Figure 3C:
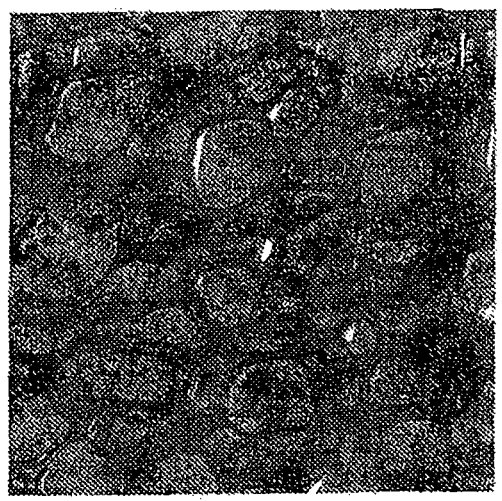

Thereafter, an OH premix is made by mixing the components as per Table 1 (amounts given for a single foam batch, and can be scaled up for more batches). For making the foams, NCO premix and OH premix are poured together in the amounts per Table 1, and mixed vigorously in a Flacktek (or equivalent mixer) for 10 sec at 3400 rpm speed. Then Enovate is added to the foaming solution and mixed again for 5 sec at 3400 rpm in Flacktek mixer. The solution is then transferred to the oven at 90° C. and allowed to rise up. Cell structures of resulting foams are shown in FIGS. 3A, 3B and 3C. Cell structure of low density degradable shape memory polymer foams made from polycaprolactone triol, triethanol amine, water (chemical blowing agent) and hexamethylene diisocyanate. Densities in range of 0.020-0.025 g/cc are achieved. Scale bar=200 um. FIG. 3A shows EA0PCT100FW96, (0% TEA @ 0.45 OH/NCO). FIG. 3B shows TEA30PCT70FW96 (30% TEA @0.45 premix OH/NCO). FIG. 3C shows TEA60PCT40FW96 (60% TEA @0.42 premix OH/NCO).

The order of mixing the components together, mixing durations and speeds, cure temperature and conditions can be changed with similar results.

TABLE 1

Foam formulation for the synthesis of degradable foams involving Polycaprolactone triol (PCT), Triethanol amine (TEA), water, as chemical blowing agent, and Hexamethylene diisocyanate (HDI). Surfactants DC-I990 and DC-5169, and catalysts BL-22 and T-131, as received from Air Products, Inc. are used. Actual weights of chemicals added in grams are given.

| | NCO premix | | | OH Premix | | | | | | | Foam | | |
|---|---|---|---|---|---|---|---|---|---|---|---|---|---|
| | PCT (g) | TEA (g) | HDI (g) | PCT (g) | TEA (g) | Water (g) | DC-I990 (g) | DC-5169 (g) | BL-22 (g) | T-131 (g) | NCO premix (g) | OH Premix (g) | Envte * (ml) |
| 1 | 32.12 | 0 | 60 | 2.48 | 0 | 0.92 | 1.3 | 1.5 | .253 | .101 | 32 | 6.55 | 3 |
| 2 | 22.48 | 4.79 | 60 | 1.83 | 0.39 | 0.97 | 1.3 | 1.5 | .253 | .101 | 32 | 6.34 | 3 |
| 3 | 11.99 | 8.94 | 60 | 1.47 | 1.09 | 1.04 | 1.3 | 1.5 | .253 | .101 | 32 | 6.76 | 3 |

General Embodiment 2: Method of Controlling the Cell Structure of Polymer Foams by Controlling the Shear and/or Elongational Prepolymer Viscosity, Changing Speed/Duration/Order of Mixing of Components, Use of Nucleating Agents, Optimizing Amount and Type of Surfactants and Catalysts.

The cell structure of the foams made from the polymer composition described above may be achieved by control over the viscosity of excess isocyanate prepolymer. A larger cell size is obtained at lower viscosity of prepolymer and as the viscosity is increased, the cell size gradually decreases. By adding a higher amount of hydroxyl monomer in the prepolymer, the viscosity can be manipulated while still keeping the net composition of the polymer the same. Hence finer control of foam cell structure is possible. This technique is based on the fact that at a lower viscosity of the prepolymer, the rate of drainage of the polymer solution from the foam cell lamella is higher, and also the resistance to foam cell expansion with a given internal bubble pressure is lower, for a longer period of time until the gelation of the polymer occurs. Apart from changing the ratio of hydroxyl to isocyanate groups in the prepolymer, the viscosity can also be manipulated by adding some inert liquid phase solvents in the system.

EXAMPLE 3

Foams with controlled cell structure were made by using Hydroxy propyl ethylene diamine, Triethanol amine as the hydroxyl monomers, and Hexamethylene diisocyanate. The viscosity of the foaming solution was varied to achieve a controlled change in cell structure of the foams.

First an NCO premix, or prepolymer with excess diisocyanate, is made by mixing the components as per Table 2. Since this composition readily forms a single phase solution, very vigorous mixing is not required. Using a mechanical vortex or shaking by hand worked well for creating a clear solution. The NCO premix is then allowed to cure over a period of 2-3 days. The viscosity of the solution increases as reaction between hydroxyl and isocyanate groups takes place reaching a value in the range of 2-60 Pa's for various formulations in Table 2 (viscosity values shown in FIG. 4).

Thereafter, an OH premix is made by mixing the components as per Table 2 (amounts given for a single foam batch, and can be scaled up for more batches).

Figure 4:
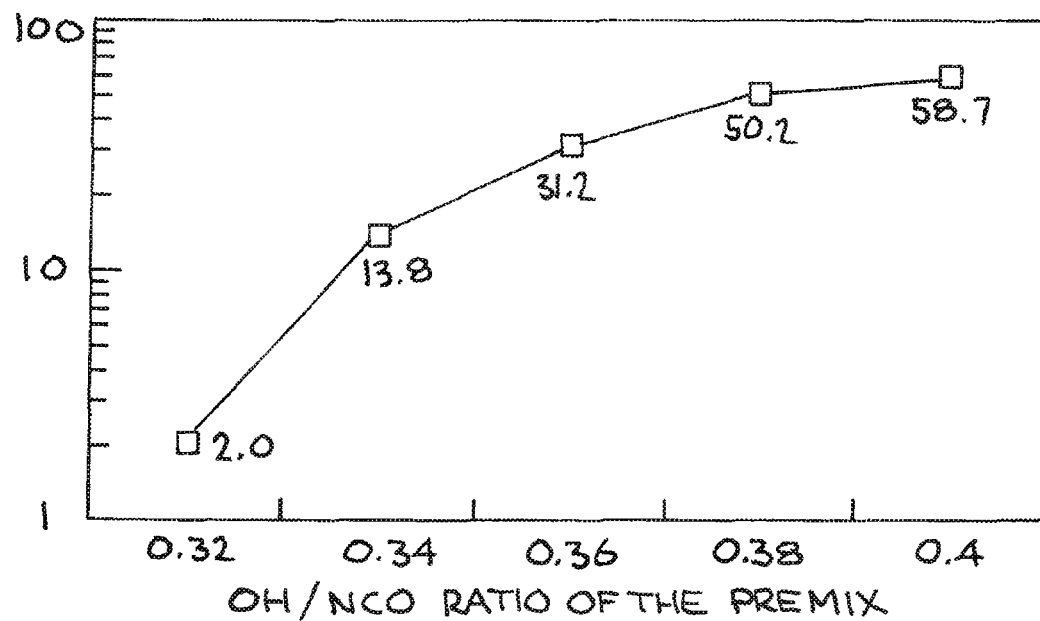
FIG. 4 is a graphical plot showing the "Trend of variation in the prepolymer rheology with increase in the OH/NCO ratio of the prepolymer".

For making the foams, NCO premix and OH premix are poured together in the amounts per Table 2, and mixed vigorously in a Flacktek (or equivalent mixer) for 10 sec at 3400 rpm speed. Then Enovate is added to the foaming solution and mixed again for 5 sec at 3400 rpm in Flacktek mixer. The solution is then transferred to the oven at 90° C. and allowed to rise up. Cell structure is shown in FIG. 4.

The order of mixing the components together, mixing durations and speeds, cure temperature and conditions can be changed with similar results.

FIGS. 5A, 5B, 5C, 5D, 5E and 5F show variation in cell structure achieved based on the viscosity of the foaming prepolymer. Variation in cell structure is achieved based on the viscosity of the foaming prepolymer. The net formulation of 44% Hydroxy Propyl Ethylene Diamine, 11% Triethanol Amine and 41% water, based on % equivalents, was used with Hexamethyene diisocyante at 104 isocyanate index for all cases. Scale bar=400 um.

TABLE 2

Foam Formulation for varying the viscosity of the foaming solution in order to obtain controlled variation in cell structure.

| | NCO premix | | | OH Premix | | | | | | | Foam | | |
|---|---|---|---|---|---|---|---|---|---|---|---|---|---|
| | HPED (g) | TEA (g) | HDI (g) | HPED (g) | TEA (g) | Water (g) | DC-I990 (g) | DC-5169 (g) | BL-22 (g) | T-131 (g) | NCO premix (g) | OH Premix (g) | Enovate (ml) |
| 1 | 16.690 | 2.839 | 80.000 | 4.472 | 0.761 | 1.130 | 1.3 | 1.5 | .253 | .101 | 32 | 9.516 | 3 |
| 2 | 17.803 | 3.028 | 80.000 | 4.061 | 0.691 | 1.115 | 1.3 | 1.5 | .253 | .101 | 32 | 9.021 | 3 |

TABLE 2-continued

Foam Formulation for varying the viscosity of the foaming solution in order to obtain controlled variation in cell structure.

| | NCO premix | | | OH Premix | | | | | | | Foam | | |
|---|---|---|---|---|---|---|---|---|---|---|---|---|---|
| | HPED (g) | TEA (g) | HDI (g) | HPED (g) | TEA (g) | Water (g) | DC-I990 (g) | DC-5169 (g) | BL-22 (g) | T-131 (g) | NCO premix (g) | OH Premix (g) | Enovate (ml) |
| 3 | 18.916 | 3.217 | 80.000 | 3.661 | 0.623 | 1.101 | 1.3 | 1.5 | .253 | .101 | 32 | 8.538 | 3 |
| 4 | 20.028 | 3.406 | 80.000 | 3.270 | 0.556 | 1.087 | 1.3 | 1.5 | .253 | .101 | 32 | 8.067 | 3 |
| 5 | 21.141 | 3.596 | 80.000 | 2.890 | 0.491 | 1.073 | 1.3 | 1.5 | .253 | .101 | 32 | 7.609 | 3 |
| 6 | 22.254 | 3.785 | 80.000 | 2.518 | .428 | 1.060 | 1.3 | 1.5 | .253 | .101 | 32 | 7.161 | 3 |

Surfactants DC-I990 and DC-5169, and catalysts BL-22 and T-131 are used as received from Air Products, Inc. Actual weights of chemicals added in grams are given.

Variation in the duration and speed of mixing the foaming solution is another method of controlling the cell structure of foams disclosed here. A higher duration or speed of mixing of the foaming solution gives finer cell size with denser foams because the forces acting on the material during mixing can break up the larger bubbles. Further, due to the viscous heating during mixing, part of the blowing gas can be lost, and also the reaction can speed up causing gelation to occur faster. This leaves less time for the foam to blow up causing denser foams with smaller cell structure. As the mixing time is reduced on the other extreme, the foam structure can be non-uniform or the foams can eventually collapse due to phase separation of hydroxyl and isocyanate moieties, and their inability to react fast enough. For very immiscible monomers, if collapse is still seen at relatively high mixing durations, the addition of the hydroxyl premix can be done in two steps, a) First mixing the balance hydroxyl monomers with the isocyanate premix for longer time on the order of a few minutes, b) then catalysts, water and physical blowing agents added to foaming solution and mixed for a shorter time on the order of a few seconds.

Increase in the amount of surfactants and/or catalysts can also help in decreasing the cell size by increasing the stabilization of the cells and increasing the rate of reaction respectively.

General Embodiment 3: Method of Making Extremely Low Density Foams (Up to 0.005 g/Cc) Using Co-blowing Agents and Other Related Methods.

Figure 6:
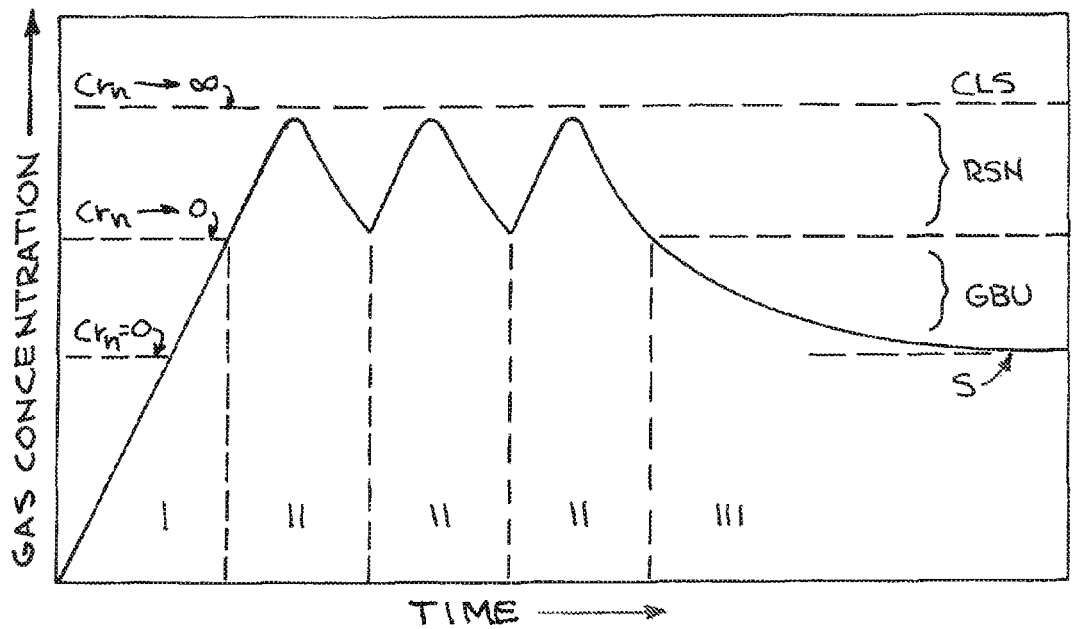
FIG. 6 is a graphical plot illustrating the mechanism of obtaining lower density foams via use of successively higher boiling point blowing agents.

Foams of very low density (as low as 0.005 g/cc), are made by use of successively higher boiling point blowing agents. This strategy is based on the process of foam blowing. For a pure liquid, formation of foam cells during blowing is dependent on the concentration of gas present in the foaming solution at any given time. As the gas concentration increases, it is only above a critical concentration that Rapid Self Nucleation (RSN) begins to occur—see Klempner, D., Sendijarevic, V., Sendijarevi c, V. & Aseeva, R. M. *Handbook of polymeric foams and foam technology*. (Hanser Gardner Publications, 2004) and LaMer, V. Kinetics in phase transitions. *Industrial & Engineering Chemistry* 44, 1270-1277 (1952), (FIG. 6). As the gas is used up in formation of cells, its concentration gradually decreases below the critical concentration required for self nucleation. Beyond this point, diffusion of the gas in the already existing bubbles leads to Growth of the bubbles By Diffusion (GBD), i.e. increase in foam cell size. If the concentration reaches the Critical Limiting Super saturation (CLS) the excess gas will spontaneously form larger voids. Hence by being able to increase the concentration of gas in the foaming solution at regular intervals, we can control its concentration in RSN range and increase the number of cells, rather than increasing the cell size or allowing development of voids. This results in foams with lower densities while maintaining a high modulus of foams, without formation of large voids/holes. Some options for such blowing agents include HFC 245-fa (Boiling Point 15.3° C.), Micro care CF: Blend of 40% HFC 365-mfc and 60% HFC 4310-mee (Boiling Point 45° C.) and HFE 7100 (Boiling Point 61° C.). While this method decreases the density of the foam by introduction of higher amount of gas phase, the cell structure can also get changed in this process leading to larger cells because of a higher gas pressure inside the cells. For maintaining a small cell size, simultaneous increase in the surfactant levels needs to be done to decrease the surface tension and stabilize the small cell size. Instead of using multiple blowing agents, a process of introducing a given blowing agent to the foaming solution, at specified time intervals, can also be engineered with the same result.

Use of particulate nucleating agents is another way in which we can catalyze the generation of bubbles and potentially lower the possibility of formation of voids or large increase in cell size. Adding leachable porogens such as salt, to the foaming solution in conjunction with the physical and chemical blowing agents, can work in this direction. Here the presence of porogens can assist in keeping the individual cell size from growing larger, both by nucleation of bubbles, and by increasing the viscosity of the foaming solution. Also, they can be leached out of the foam post cure, further lowering the foam bulk density.

Another foam processing technique that can achieve densities down to 0.005 g/cc, while maintaining a good shape memory behavior, is to pull vacuum on the foam while the foam is rising, and allow it to cure under vacuum.

Applying vacuum counters the effect of gravity and assists in a better expansion of the foam, leading to lower densities. The time of pulling vacuum during foaming can be changed to manipulate the cell size and density: vacuuming too soon in the foaming process gives larger cells and lower density; vacuuming much later in the foaming process gives finer cells with relatively higher density. This technique can potentially be used in conjunction with other methods of using leachable porogens, nucleating agents and adjustment of surfactant levels etc. to simultaneously control the cell structure.

Another technique for making highly crosslinked low density foams is to use two or higher functionality carboxylic acids in place of water as the blowing agent. One carboxylic acid group reacts with one isocyanate group to release a carbon-dioxide molecule while forming an amide bond. This is twice the production of blowing gas compared to water with the same amount of isocyanate, making it a promising technique. Further higher functionality of carboxylic acids, such as Citric Acid, form covalent crosslinks in the foam, as opposed to physical crosslinks with urea from the use of water, and assist in making a highly covalently crosslinked network structure per our material design criteria. This further entails the ability to significantly increase the concentration of carboxylic acid based chemical blowing agents in the foam formulation without affecting the network structure of the material, which is not possible with use of water. This gives an important handle in reducing the foam bulk density while maintaining a high density of covalent crosslinks in the material network structure.

General Embodiment 4: Methods of Optimization of the Physical Properties Such as Porosity, Cell Size and Distribution, Cell Openness Etc. Of these Materials, to Further Expand their Uses and Improve their Performance.

Density/porosity of the materials can be controlled either for a specific density/porosity, or a continuous gradient or another pattern in the variation density/porosity across a sample. This can be done e.g. by using one or more of the techniques in the method 3) above on a single piece of foam, and/or by combining different foams of varying density/porosity gradients as desired.

Similarly the cell size and cell size distribution of a foam sample can be engineered, e.g. by using one or more of the methods in the 2) above on the same foam, and/or by combining different foams of varying cell sizes and distribution to achieve respective gradients as desired.

Again the degree of cell openness of the foams can be controlled, for e.g. via changing the synthesis process, such as the amount and type of surfactants and catalysts etc. or using post processing methods for removal of membranes, such as hydrolysis, oxidation, heat or mechanical treatment etc.

By exercising control of one or more of density/porosity, cell size, cell size distribution, cell openness etc. with a desired pattern of variation of respective properties throughout the bulk of the material, the material can be optimized for use in multiple applications. For e.g. when a foam sample is actuated in a media, the rate of diffusion of the media in the foam can be controlled by controlling the density/cell sizes/cell openness etc. throughout the foam sample.

Improved cell opening is achieved, in another embodiment by the use of high z metal nano- or micro-particles, including but not limited to tungsten, tantalum, platinum and, palladium. These particles can serve the dual purpose of a) assisting in the cell opening during the foaming process, and/or b) providing x-ray contrast for imaging in the foam devices.

Metals typically have a surface oxide layer which provides them with a high surface energy and therefore allowing them to be wetting with the foam formulation. A surface modification of the metal particles with a low surface energy coating such as a fluorinated coupling agent (e.g. fluorosiloxane, fluorosilane, fluorocarbon, fluoropolymer) helps to destabilize the membrane during the foaming process by decreasing the extent of its wetting with the foaming solution.

Mechanical surface treatment of the metal particles, such as roughening, is another method to enhance their ability to open cells (and reduce adhesion of the PU foam to the particles). It is known that liquid repellent surfaces of high surface energy materials can simply be made by having nano-scale grooves or other types of roughness (possibly pillars) in the surface. Particle surface roughness can also affect the ability of the foam formulation to wet the particle surface, and enhance foam cell membrane destabilization, in the same way.

The size of the particulate is another important parameter since the particles may be more effective in destabilizing the foam cell membranes as the membrane thickness approaches particle size. Selection of the particle size can be used to tune the specific area at which the membranes are destabilized during foaming. The onset of destabilization is expected to occur approximately at the point when particle size equals membrane thickness.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A shape memory polymer composition comprising:
at least two units, each comprising three or more branches; wherein (a) at least one of the branches comprise an ester, and (b) at least some of the at least two units are crosslinked to others of the at least two units through linkages comprising urethane;
wherein at least one of the at least two units comprises a derivative of citric acid;
wherein the at least one of the branches comprises a derivative of an aliphatic diol;
wherein the urethane comprises a derivative of diisocyanate and the diisocyanate is selected from a group consisting of: hexamethylene diisocyanate (HDI), trimethyl hexamethylene diisocyanate, isophorone diisocyanate, toluene diisocyanate, and methylene diphenyl diisocyanate.

2. The polymer composition of claim 1, wherein the polymer composition is biodegradable.

3. A shape memory foam comprising the polymer composition of claim 2.

4. A shape memory polymer composition comprising at least two units; wherein (a) at least one of the at least two units comprises three or more branches, (b) at least one of the three or more branches comprises an ester, and (c) each of the at least two of units is crosslinked to another of the at least two units with a linkage comprising urethane, wherein the urethane is a derivative of hexamethylene diisocyanate;
wherein at least one of the at least two units comprises a derivative of Triethanol amine (TEA);
wherein at least one of the three or more branches comprises a derivative of 3-Hydroxybutyrate.

5. The polymer composition of claim 4, wherein the polymer composition is biodegradable.

6. A shape memory foam comprising the polymer composition of claim 5.

7. The polymer composition of claim 1,
wherein another one of the at least two units comprises a derivative selected from the group consisting of: Triethanol amine (TEA), Hydroxy propyl ethylene diamine (HPED), Glycerol, Pentaerythritol, Bis-tris methane, Bis-tris propane, 1,2,4 Butane triol, Miglitol, Trimethylolethane, and Tris(hydroxymethyl)aminomethane;
wherein another one of the branches comprises a derivative selected from the group consisting of: 3-Hydroxybutyrate, Lactic acid, and Glycolic acid.

8. The polymer composition of claim 1, wherein the urethane comprises a derivative of diisocyanate and the diisocyante is selected from a group consisting of: tri-methyl hexamethylene diisocyanate, isophorone diisocyanate, toluene diisocyanate, and methylene diphenyl diisocyanate.

9. The foam of claim 3 having a portion of the foam with a density of between 0.025 g/cc and 0.005 g/cc.

10. The foam of claim 6 having a portion of the foam with a density of between 0.025 g/cc and 0.005 g/cc.

* * * * *